United States Patent [19]

Witt et al.

[11] 4,241,183

[45] Dec. 23, 1980

[54] STARCH LIQUEFACTION PROCESS

[75] Inventors: Paul R. Witt; Richard D. Harvey, both of Muscatine, Iowa

[73] Assignee: Grain Processing Corporation, Muscatine, Iowa

[21] Appl. No.: 34,333

[22] Filed: Apr. 30, 1979

[51] Int. Cl.³ .............................................. C12P 19/22
[52] U.S. Cl. ............................................ 435/95; 435/99
[58] Field of Search ............................ 435/93, 95, 99

[56] References Cited

U.S. PATENT DOCUMENTS

| | | | |
|---|---|---|---|
| 3,720,583 | 3/1973 | Fisher | 435/95 |
| 4,073,947 | 2/1978 | Witt | 426/16 X |
| 4,092,434 | 5/1978 | Yoshizumi et al. | 435/93 X |

*Primary Examiner*—Lionel M. Shapiro
*Attorney, Agent, or Firm*—Neuman, Williams, Anderson & Olson

[57] ABSTRACT

A malt source of enzymes is used to liquefy starch at high temperatures.

3 Claims, No Drawings

STARCH LIQUEFACTION PROCESS

This invention relates to the use of malt or malt infusions to reduce the viscosity of starch pastes.

It is well known that malted cereal grains, such as malted wheat, oats, rye, triticale and barley, contain the enzyme, alpha-amylase, which is capable of hydrolyzing starch molecules to produce starch fractions that are less viscous in aqueous solutions than the cooked native starch. Thus, it is possible to prepare aqueous starch solutions containing much higher solids levels with liquefied starch than is possible with cooked native starch. This is important in many applications. For example, in brewing beer, starch can be cooked in a cereal cooker, then cooled and added to an aqueous slurry of ground malt in the mash tub for conversion to fermentable sugars by the action of alpha-amylase and beta-amylase in the malt. Malt infusion may be added to the cereal cooker to liquefy the starch adjunct, but due to the heat lability of the enzymes, this is usually done at about 50° C. and fairly low levels of adjunct are used because of the high viscosity of the cooked starch at 50° C. Generally, the starch concentration in such preparations does not exceed about 20% solids so as to maintain the viscosity at a level low enough that it can be handled. Due to the dilatant character of starch pastes, it is generally recognized that a starch solids level of about 40% is about the highest concentration that can be pasted in conventional equipment. This paste must then be hydrolyzed with acids or enzymes to reduce its viscosity so that it can be subsequently handled. It is well recognized that enzymes are proteins and therefore are denatured at elevated temperatures. Therefore, it is common practice in batch starch conversion processes to add alpha-amylase to the starch before the starch slurry reaches the gelatinization temperature and then add a second quantity of the enzyme after the starch paste has been cooled to about 65° C. or below because of the instability of the enzyme at higher temperatures. The maximum temperature for malt alpha-amylase activity is generally understood to be about 80° C. with the enzyme being rapidly inactivated at temperatures above 80° C. Thus, in *A Textbook of Brewing*, Vol. 1, Chapman & Hall, Ltd., London, 1957 it is stated on page 275: "78°-80° C. is the maximum temperature at which liquefying alpha-amylase is still active and also the temperature at which nearly every cereal starch is gelatinized."

It is known that various enzymes of bacterial origin can withstand higher temperatures without inactivation than malt-derived enzymes, but for aesthetic reasons and labeling problems attendant to their use, brewers and others are reluctant to use bacterial enzyme preparations in their operations. Also, malt has the further advantage of containing, in addition to the alpha-amylase, beta-amylase which converts liquefied starch to maltose, whereas the microbial alpha-amylase preparations only liquefy the starch.

Very unexpectedly, we have now found that malt or a malt infusion can be added to cooked starch pastes at high temperatures, that is, at temperatures above 75° C., to achieve liquefaction with high starch solids levels, such as 40%, dry solids basis. The starch slurry can be cooked or pasted in a batch cooker or in a continuous cooker. With the use of a continuous cooker which provides sufficient holding time, higher solids starch slurries than were previously possible can be cooked and liquefied continuously with malt enzymes at high temperatures without the necessity of cooling the paste to a temperature significantly lower than the gelatinization temperature of the starch. For example, a high solids starch slurry can be cooked and liquefied at a high temperature to provide an adjunct that may be added directly to a mash tub enabling the brewer to prepare higher solids worts than was possible heretofore. The invention is not limited to use in brewery operations, but is useful in any application where it is desired to liquefy starch pastes with malt enzymes such as, e.g., in the preparation of breakfast cereals, malt flavored beverages, and in the production of high maltose corn syrup which has application in the bakery and confectionery fields.

An important object of the invention is to provide a process for liquefying high solids content starch pastes using malt-derived enzymes.

Another object is to provide a process for reducing the viscosity of high solids starch pastes so that the starch pastes can be readily handled in conventional transfer equipment.

Still another object is to provide a process for treating starch pastes with malt-derived enzymes at high temperatures whereby the set-back and starch retrogradation which normally occur on cooling of the starch paste are reduced to a minimum.

A further object is to provide a process for liquefying starch pastes at high temperatures to prevent the formation of amylose-lipid complexes that form at the lower temperatures conventionally used for starch paste liquefaction.

These and other objects will be apparent from the following description of the invention.

The process of the present invention comprises cooking an aqueous slurry of starch to gelatinize and paste the starch. Gelatinization or pasting of starch can be accomplished by slurrying the starch in water, adjusting the pH to 5.0 to 8.0, preferably 6.0 to 7.0, and heating the slurry to a temperature above about 75° C. in any suitable cooking equipment. The starch concentration of the starch slurry can be as high as can be handled by the cooker employed. Generally, this level is about 40% starch solids, although certain cookers are capable of handling higher starch concentrations. After cooking and pasting of the starch, the slurry can be cooled, if necessary, and a source of malt enzyme added to the starch paste. The mixture is then held, preferably with agitation, at a temperature above 75° C., preferably at a temperature of about 85° to 95° C., for a time sufficient to liquefy or to reduce the viscosity of the starch paste to a desired degree. The liquefying time will depend on the enzyme activity of the malt enzyme source, the temperature, pH and solids concentration of the starch paste and the desired degree of liquefaction. Liquefaction to reduce the viscosity of the starch paste to a suitable value, generally not substantially above about 1500 centipoise, which permits handling of the paste is generally accomplished in periods ranging from 2 to 30 minutes. Higher liquefaction temperatures are preferred since the more the temperature of the starch paste is reduced the more difficult and cumbersome becomes the handling thereof. Also, starch retrogradation is a progressive problem which is accelerated by reducing the temperature of starch pastes.

As is well known in the art, a source of calcium ions is helpful in the stabilization of alpha-amylase. Accordingly, an appropriate level of a calcium source such as calcium acetate, calcium chloride, calcium hydroxide, and the like, optionally can be added to the malt enzyme source or to the starch. Calcium affords two competing effects in that it stabilizes alpha-amylase against temperature inactivation and it inhibits the activity of the enzyme. At low concentrations, the inhibition is so low that the inhibitory effect of calcium is not appreciably noticeable, but its stabilizing effect is evident. At higher concentrations the inhibitory effect on the enzyme activity is greater than the stabilization effect so that the degree of liquefaction is reduced as compared to that achieved with the use of lower amounts of calcium. Thus, it is generally preferred to use calcium in low concentrations, such as on the order of about 0.004 or less grams of calcium per gram of malt infusion solids.

Ground malt or malt flour or a malt infusion (malt extract) can be used as a source of the malt enzymes. Brewers may advantageously use a portion of the extract (malt infusion) obtained from malt in the course of wort production. Alternatively, a malt infusion can be prepared by coarsely grinding malt to give about the following screen profile.

|  | % Meal |
|---|---|
| On U.S. No. 10 mesh screen | 38.0 |
| On U.S. No. 16 mesh screen | 33.9 |
| On U.S. No. 30 mesh screen | 15.0 |
| On U.S. No. 60 mesh screen | 6.0 |
| On U.S. No. 100 mesh screen | 2.8 |
| Thru No. 100 mesh screen | 4.3 |

The ground malt is slurried in water at 50° C. to give about 30% ground (whole) malt solids and held with periodic stirring for about 30 minutes. The slurry is filtered through cloth and allowed to stand until the suspended solids settle.

The starch which is to be treated can be derived from any conventional starch source, such as corn, potato, tapioca, wheat, sago, rice and the like. The malt enzyme source can be malt itself, such as ground malt or malt flour, or it can be a malt infusion which is a water extract of malt. The malt enzyme source is employed in an amount to provide at least about 1.0 SKB units of alpha-amylase per gram of starch. An SKB unit of enzyme activity is determined by the assay method of Sandstedt, R. M., Kneen, E. and Blish, M. J., described in *Cereal Chemistry* 16, 712-723 (1939).

The following examples further illustrate the invention and the advantages thereof. In the following examples the general procedure employed involved slurrying starch in tap water to a solids level of 40% starch, dry solids basis (except Example VI). The pH of the slurry was adjusted as indicated and calcium added as indicated. The starch slurry was then cooked by passing it through a continuous starch cooker. The continuous starch cooker used was a Thermal/Chemical Converter, which is the tradename of a continuous starch cooker available from Grain Processing Corporation. After cooking, the starch paste was cooled by agitated countercurrent cooling to the temperatures indicated. A malt infusion which contained 12.77% solids and 62.5 SKB units of alpha-amylase per milliliter was added to give the indicated enzyme concentration and the mixture was held with moderate stirring to effect liquefaction. Brookfield viscometer readings were taken at the times indicated. The conditions of starch treatment used in the following examples can be summarized as follows:

| Example No. | Starch Concentration | Starch pH | Ca In Starch | Enzyme Level* | Ca In Malt | Conversion Temperature(s) |
|---|---|---|---|---|---|---|
| I | 40% | 6.5 | 0.04% | 0.55, 1.1 & 2.2 | 0 | 90° |
| II | 40 | 6.0 | 0 | 1.1 | 0-0.6% | 80°-95° C. |
| III | 40 | 6.5 | 0 | 1.1 | 0 & 0.2% | 75°-100° C. |
| IV | 40 | 7.0 | 0 | 1.1 | 0 & 0.2% | 80°-95° C. |
| V | 40 | 6.5 | 0.04% | 1.1 | 0 & 0.2% | 80°-95° C. |
| VI | 31.8 | 6.0 | 0.04% | 1.1 | 0 & 0.2% | 80°-95° C. |
| VII | 40 | 6.0 | 0 | 1.1 | 0 & 0.2% | 70°-90° C. |
| VIII | 40 | 6.0 | 0 | 1.1 | 0 | 90° C. |

*SKB units of alpha-amylase/gram of starch

EXAMPLE I

In this example a water slurry of starch was adjusted to a pH of 6.5 and cooked. The starch contained 0.04% added calcium and no calcium was added to the malt infusion. Liquefaction was conducted by holding the cooked starch paste at a temperature of 90° C. using enzyme levels as indicated. The results were as follows:

| Malt Infusion Added | | Liquefaction Time, Min. | | | |
|---|---|---|---|---|---|
| Milliliters/800 gm Starch Slurry | SKB Units Alpha-amylase/gm Dry Starch | 0 | 10 | 20 | 30 |
| | | Brookfield Viscosity, cps. (100/RPM) | | | |
| 0 | 0 | 96,000* | | | 65,000* |
| 2.8 | 0.55 | | 3,380 | 1,886 | 1,892 |
| 5.6 | 1.10 | | 2,696 | 1,360 | 1,328 |
| 11.2 | 2.20 | | 364 | 236 | 213 |

*Run at 20 RPM because it could not be measured at 100 RPM

The results show that an amount of malt infusion sufficient to provide 1.10 SKB units of alpha-amylase/gram of dry starch was sufficient to liquefy the starch sufficiently for commercial handling, maximum 1500 centipoise, in less than 20 minutes. Holding at 90° C. with 2.2 SKB units of alpha-amylase accomplished greater liquefaction in less than 10 minutes. Liquefaction of the starch paste at a temperature of 90° C. minimizes the cooling required after cooking or pasting and simplifies processing of the starch paste.

EXAMPLE II

In this example a water slurry of starch was adjusted to pH 6.0 and cooked. The starch did not contain any added calcium, but calcium was added to the malt infusion as indicated. Liquefaction was conducted at temperatures of 80°, 90° and 95° C. using 1.1 SKB units alpha-amylase per gram of dry starch. The results obtained were as follows:

| Temperature °C. | Ca as % of Malt Solids | Liquefaction Time, Min. 10 | 20 | 30 |
|---|---|---|---|---|
| | | Brookfield Viscosity, cps. (100 RPM) | | |
| 95 | 0 | 9,600 | 8,120 | 8,110 |
| | 0.2 | 7,440 | 9,220 | 15,600 |
| | 0.4 | 12,880 | 17,600 | 16,240 |
| | 0.6 | 20,080 | 24,360 | 26,200 |
| 90 | 0 | 1,724 | 1,180 | 960 |
| | 0.2 | 900 | 898 | 750 |
| | 0.4 | 1,434 | 1,278 | 1,126 |
| | 0.6 | 1,566 | 1,450 | 1,242 |
| 80 | 0 | 541 | 405 | 259 |
| | 0.2 | 532 | 314 | 260 |
| | 0.4 | 705 | 298 | 224 |
| | 0.6 | 266 | 320 | 256 |

EXAMPLE III

In this example a water slurry of starch was adjusted to pH 6.5 and cooked. The starch did not contain any added calcium but calcium was added to the malt infusion as indicated. Liquefaction was conducted at temperatures of 75° C., 80° C., 85° C., 90° C., 95° C. and 100° C. using 1.1 SKB units alpha-amylase per gram of starch. The results obtained were as follows:

| Temperature °C. | Ca as % of Malt Solids | Liquefaction Time, Min. 10 | 20 | 30 |
|---|---|---|---|---|
| | | Brookfield Viscosity, cps. (100 RPM) | | |
| 100 | 0 | 14,200 | 18,160 | 23,500 |
| | 0.2 | 7,920 | 8,380 | 6,710 |
| 95 | 0 | 9,220 | 6,880 | 7,330 |
| | 0.2 | 3,332 | 2,912 | 3,020 |
| 90 | 0 | 1,000 | 682 | 299 |
| | 0.2 | 682 | 578 | 452 |
| 85 | 0 | 322 | 302 | 279 |
| | 0.2 | 476 | 390 | 345 |
| 80 | 0 | 308 | 195 | 162 |
| | 0.2 | 780 | 463 | 297 |
| 75 | 0 | 2,390 | 286 | 158 |
| | 0.2 | 420 | 283 | 238 |

EXAMPLE IV

In this example a water slurry of starch was adjusted to pH 7.0 and cooked. The starch did not contain any added calcium but calcium was added to the malt infusion as indicated. Liquefaction was conducted at temperatures of 80° C., 90° C. and 95° C., using 1.1 SKB units alpha-amylase per gram of starch. The results obtained were as follows:

| Temperature °C. | Ca as % of Malt Solids | Liquefaction Time, Min. 10 | 20 | 30 |
|---|---|---|---|---|
| | | Brookfield Viscosity, cps. (100 RPM) | | |
| 95 | 0 | 25,280 | 36,840 | 28,160 |
| | 0.2 | 20,400 | 40,000 | 40,000 |
| 90 | 0 | 1,920 | 2,416 | 2,868 |
| | 0.2 | 2,652 | 1,812 | 1,952 |
| 80 | 0 | 1,470 | 460 | 283 |
| | 0.2 | 651 | 484 | 291 |

EXAMPLE V

In this example a water slurry of starch was adjusted to pH 6.5 and cooked. The starch contained 0.04% added calcium (0.128 grams in 800 grams of 40% dry starch slurry) and calcium was added to the malt infusion as indicated (an additional 0.00143 grams in 800 grams of 40% dry starch slurry). Liquefaction was conducted at temperatures of 80° C., 90° C. and 95° C., using 1.1 SKB units alpha-amylase per gram of dry starch. The results obtained were as follows:

| Temperature °C. | Ca as % of Malt Solids | Liquefaction Time, Min. 10 | 20 | 30 |
|---|---|---|---|---|
| | | Brookfield Viscosity, cps. (100 RPM) | | |
| 95 | 0 | 2,600 | 2,468 | 2,560 |
| | 0.2 | 2,340 | 2,952 | 5,300 |
| 90 | 0 | 2,696 | 1,360 | 1,328 |
| | 0.2 | 3,280 | 1,282 | 1,150 |
| 80 | 0 | 3,490 | 590 | 366 |
| | 0.2 | 1,058 | 438 | 342 |

EXAMPLE VI

In this example a 31.8% solids slurry of starch in water was adjusted to pH 6.0 and cooked. The starch contained 0.04% added calcium and calcium was added to the malt infusion as indicated. Liquefaction was conducted at temperatures of 80° C., 90° C. and 95° C. using 1.1 SKB units of alpha-amylase per gram of dry starch. The results obtained were as follows:

| Temperature °C. | Ca as % of Malt Solids | Liquefaction Time, Min. 10 | 20 | 30 |
|---|---|---|---|---|
| | | Brookfield Viscosity, cps. (100 RPM) | | |
| 95 | 0 | 5,800 | 4,930 | 4,910 |
| | 0.2 | 4,080 | 5,060 | 5,280 |
| 90 | 0 | 2,364 | 1,880 | 1,696 |
| | 0.2 | 1,892 | 2,000 | 2,064 |
| 80 | 0 | 174 | 131 | 119 |
| | 0.2 | 182 | 131 | 129 |

The results show that the addition of calcium to the starch rather than to the enzyme was more beneficial at 90° C. and 95° C. but appeared to have little effect at 80° C. and illustrate the heat stabilizing effect of the relatively high amount of calcium in the starch slurry.

EXAMPLE VII

In this example a slurry of starch in water was adjusted to pH 6.0 and cooked. The starch did not contain added calcium but calcium was added to the malt infusion as indicated. Liquefaction was conducted at temperatures of 70° C., 80° C. and 90° C. using 1.1 SKB units of alpha-amylase per gram of dry starch. The results obtained were as follows:

| Temperature °C. | Ca as % of Malt Solids | Liquefaction Time, Min. 2 | 6 | 12 | 20 |
|---|---|---|---|---|---|
| | | Brookfield Viscosity, cps. (100 RPM) | | | |
| 90 | 0 | 2,940 | 2,092 | 1,808 | 1,824 |
| | 0.2 | 1,384 | 746 | 496 | 424 |
| 80 | 0 | 4,110 | 902 | 613 | 417 |
| | 0.2 | 908 | 302 | 180 | 150 |
| 70 | 0 | — | 33,840 | 4,500 | 1,186 |

The results show that at liquefaction at 80° C. with calcium added to the malt produced the lowest viscosities in the shortest time. The high viscosity at the 70° C. liquefaction after 6 minutes illustrates the setback phenomenon due to cooling and is indicative of the problem associated with malt alpha-amylase when the starch paste is cooled to a normal operating temperature.

EXAMPLE VIII

A 40% dry solids starch paste at pH 6.0 was prepared by continuous cooking. The paste was cooled to 90° C. and a malt infusion at a level of 1.1 SKB units per gram starch was added. The mixture was held for 30 minutes with moderate stirring followed by cooling to 63° C. and an additional malt infusion was added to provide another 1.1 SKB alpha-amylase units and 3.2 beta-amylase units* per gram. The mixture was held at 63° C. for 20 minutes. The following results were obtained:

| Time of Treatment | Brookfield Viscosity, cps. (100 RPM) |
| --- | --- |
| After 30 min. at 90° C. | 485 |
| After cooling to 63° C. | 623 |
| After 20 min. at 63° C. with added enzyme | 59 |

*Malt diastatic power. Methods of Analysis, Amer. Soc. Brew. Chem., 7th Revised Ed., 1976.

The final product was assayed for carbohydrate composition by high pressure liquid chromatography and was found to contain 1.3% monosaccharides, 61.0% disaccharides, 7.8 trisaccharides, and 29.8% higher saccharides.

EXAMPLE IX

The procedure of Example VIII was repeated with the following results:

| Time of Treatment | Brookfield Viscosity, cps. (100 RPM) |
| --- | --- |
| After 30 min. at 90° C. | 2600 |
| After 20 min. at 63° C. with added enzyme | 105 |

The following carbohydrate profile was obtained:

| | |
| --- | --- |
| Monosaccharide | 1.9% |
| Disaccharides | 60.0 |
| Trisaccharides | 8.4 |
| Higher Saccharides | 29.7 |

The carbohydrate profiles of both of the starch pastes as prepared in Examples VIII and IX were ideal for use as brewer's adjunct since they are low in glucose and high in maltose as opposed to conventional starch hydrolyzates which are high in glucose.

It is seen from the foregoing that it is possible by the process of this invention to prepare high solids starch hydrolyzates that are suitable for use in various applications. Various advantages of the process are that the process permits use of an all-natural enzyme system which obviates the need to declare the presence of other enzymes on the label of the final product; slurries of maximum starch concentration can be cooked and liquefied; final starch pastes may be obtained with improved yield and quality; and set-back and retrogradation of liquefied starch are reduced to a minimum.

Those modifications and equivalents which fail within the spirit of the invention are to be considered a part thereof.

What is claimed is:

1. A process for liquefying starch which comprises adding to starch paste at a temperature above 75° C. an infusion of a malted cereal grain and holding the mixture of starch paste and infusion of malted cereal grain at a temperature above about 75° C. for a time sufficient to liquefy the starch paste to a viscosity of not substantially above about 1500 centipoise.

2. A process according to claim 1 wherein the mixture of starch paste and infusion is held at a temperature of 85°–95° C.

3. A process according to claim 1 wherein the malted cereal grain is barley malt.

* * * * *